United States Patent [19]

Urban

[11] Patent Number: 4,716,113

[45] Date of Patent: Dec. 29, 1987

[54] PROCESS FOR THE PRODUCTION OF AN (S)-METHYL OR (S)-ETHYL 4-AMINO-6-FLUOROCHROMAN-4-CARBOXYLATE

[75] Inventor: Frank J. Urban, Waterford, Conn.

[73] Assignee: Pfizer Inc., New York, N.Y.

[21] Appl. No.: 846,383

[22] Filed: Mar. 31, 1986

Related U.S. Application Data

[62] Division of Ser. No. 642,008, Aug. 20, 1984, abandoned.

[51] Int. Cl.$^4$ .................... C12P 17/06; C07P 41/00; C07D 311/04
[52] U.S. Cl. .................................. 435/125; 435/213; 435/280; 548/216; 549/404; 549/409
[58] Field of Search ................ 549/404, 409; 435/125, 435/213, 280

[56] References Cited

U.S. PATENT DOCUMENTS

| | | | |
|---|---|---|---|
| 3,878,043 | 4/1975 | Matta et al. | 435/280 |
| 4,117,230 | 9/1978 | Sarges | 548/309 |
| 4,130,714 | 12/1978 | Sarges | 548/309 |
| 4,260,684 | 4/1981 | Schutt | 435/280 |
| 4,262,092 | 4/1981 | Bauer | 435/280 |
| 4,267,342 | 5/1981 | Schnur | 548/316 |
| 4,339,589 | 7/1982 | Steglich et al. | 548/228 |
| 4,389,489 | 6/1983 | Preiss et al. | 435/280 |
| 4,435,578 | 3/1984 | Cue, Jr. et al. | 548/309 |
| 4,439,524 | 3/1984 | Schutt | 435/280 |
| 4,464,380 | 8/1984 | Hutchinson | 548/309 |
| 4,474,967 | 10/1984 | Sarges | 548/309 |

FOREIGN PATENT DOCUMENTS

| | | | |
|---|---|---|---|
| 2080304 | 2/1982 | United Kingdom | 548/309 |
| 2098212 | 11/1982 | United Kingdom | 548/309 |

OTHER PUBLICATIONS

Sakimae et al., CA 103-36173t.
G. C. Finger et al., "Aromatic Fluorine Compounds, VIII. Plant Growth Regulators and Intermediates", *Journal of the American Chemical Society*, vol. 1, p. 94, (1954).
L. F. Fieser and M. Fieser, "Reagents for Organic Synthesis," vol. 1, John Wiley and Sons, Inc., New York, N.Y., 1967, p. 1160.
J. Bryan Jones and J. F. Beck, "Techniques of Chemistry", vol. X, (Applications of Biochemical Systems in Organic Chemistry), Jones, Sik and Perlman, Editors, John Wiley & Sons, Inc., New York, N.Y., 1970, Chapter 4.
D. Ben-Ishai, et al., "A New Synthesis of N-Acyl Aromatic α-Amino Acids; Amidoalkylation of Aromatic Compounds with Glyoxylic Acid Derivatives", *Journal of the Chemical Society*, Chemical Communications, p. 349, (1975).
D. Ben-Ishai et al., "The Synthesis of p-Substituted D,L-Phenylglycines by the Amidoalkylation of Benzyl Chloride and N-Benzylamide", *Tetrahedron*, vol. 33, p. 2715, (1977).

*Primary Examiner*—Donald G. Daus
*Assistant Examiner*—Cecilia Shen
*Attorney, Agent, or Firm*—Peter C. Richardson; Lawrence C. Akers

[57] ABSTRACT

An improved process for preparing (4S)-6-fluoro-spiro-[chroman-4,4'-imidazolidine]-2',5'-dione (sorbinil) or its (2R)-methyl derivative (2-methylsorbinil) is disclosed herein, starting from p-fluorophenol in each instance. The final products obtained have known pharmaceutical value as agents for the control of certain chronic diabetic complications. Key steps concerned with the process involve converting p-fluorophenol into the appropriate β-(4-fluorophenoxy)alkane halide, followed by amidoalkylation with N-benzoyl or N-(lower alkanoyl)-α-hydroxyglycine to form an intermediate 2-amidoalkylated derivative thereof, and then dehydration and spiroalkylation of said intermediate by treatment with a dehydrating agent and a base to yield a spiroalkylated azlactone compound. The latter compound is then subsequently converted to the known 4-amino-6-fluorochroman-4-carboxylic acid or the novel (2R)-methyl derivative thereof, both in the form of their hydrohalide acid addition salts, by employing acid hydrolysis and the intermediate spiro-amino acid hydrohalide salt is thereafter converted to the corresponding methyl or ethyl ester and resolved with α-chymotrypsin to afford the desired (S)-methyl or (S)-ethyl ester. Treatment of either of these latter two esters with an alkali metal cyanate in an acid medium then effects conversion of same to the desired spiro-hydantoin ring compound. Alternatively, the spiro-amino acid hydrohalide salt can also be converted to the desired spiro-hydantoin ring compound in a known manner, involving a sequence of three reaction steps. The spiroalkylated azlactone compound of the instant invention, as well as the methyl and ethyl esters mentioned above, are themselves novel compounds and are valuable as synthetic intermediates in the process of this invention.

1 Claim, No Drawings

PROCESS FOR THE PRODUCTION OF AN (S)-METHYL OR (S)-ETHYL 4-AMINO-6-FLUOROCHROMAN-4-CARBOXYLATE

This is a division of application Ser. No. 642,008, filed on Aug. 20, 1984, and now abandoned.

BACKGROUND OF THE INVENTION

This invention relates to a new and useful process for preparing two valuable asymmetric spiro-hydantoin ring compounds. More particularly, it is concerned with an improved chemical process for synthesizing (4S)-6-fluoro-spiro-[chroman-4,4'-imidazolidine]-2',5'-dione (sorbinil) and its (2R)-methyl derivative (2-methylsorbinil), which are of especial value in the field of medicinal chemistry in view of their known ability to act as aldose reductase inhibitors and thereby effectively control certain chronic diabetic complications, such as diabetic cataracts and neuropathy, etc. The invention also includes within its scope various novel compounds which are useful as intermediates in the process.

According to the prior art, sorbinil was first reported as d-6-fluoro-spiro-[chroman-4,4'-imidazolidine]-2',5'-dione by R. Sarges in U.S. Pat. No. 4,130,714. It was originally prepared by a multi-step process which essentially involved condensing 6-fluoro-4-chromanone with potassium cyanide and ammonium carbonate to form the corresponding racemic precursor, followed by resolution of the latter dl-compound with l-brucine. The 6-fluoro-4-chromanone used in the process was ultimately derived from p-fluorophenol in a series of steps which first involved converting the latter compound to β-(p-fluorophenoxy)propionic acid according to the method described by G. C. Finger et al. in the *Journal of the American Chemical Society*, Vol. 81, p.94 (1959), followed by intramolecular condensation of the latter intermediate acid in the presence of polyphosphoric acid to effect ring-closure to the desired chromanone compound.

Later developments in the overall method of production then finally gave a process for producing sorbinil which involved the following steps, viz., (1) p-fluorophenol was first converted to β-(p-fluorophenoxy)propionitrile by treatment with acrylonitrile in the presence of Triton B; (2) the nitrile intermediate was then converted to β-(p-fluorophenoxy)propionic acid by means of hydrochloric acid; (3) β-(p-fluorophenoxy)propionic acid was then condensed in the presence of concentrated sulfuric acid at 50° C. to afford 6-fluoro-4-chromanone; (4) the latter compound was thereafter condensed with potassium cyanide and ammonium carbonate in ethanol under standard Bucherer-Berg conditions to give the racemic precursor of sorbinil, which is called dl-6-fluoro-spiro-[chroman-4,4'-imidazolidine]-2',5'-dione; (5) the latter racemic spiro-hydantoin was then hydrolyzed with aqueous sodium hydroxide to the corresponding spiro-amino acid, which is called 4-amino-6-fluorochroman-4-carboxylic acid; (6) the latter acid, which can not be conveniently isolated in the process, was then treated in situ with sodium or potassium cyanate (after first adjusting the pH of the aqueous solution) in order to convert the amino acid to the corresponding hydantoic acid, which is called 6-fluoro-4-ureidochroman-4-carboxylic acid; (7) the latter hydantoic acid was then resolved according to the method described by B. W. Cue, Jr. et al. U.S. Pat. No. 4,435,578 by treatment with l-(−)-ephedrine in aqueous methanol to form the l-(−)-ephedrine salt of (4S)-6-fluoro-4-ureidochroman-4-carboxylic acid; and (8) the latter crystalline salt was thereafter converted to sorbinil by heating the diastereoisomer in glacial acetic acid to effect conversion to the desired (4S)-6-fluoro-spiro-[chroman-4,4'-imidazolidine]-2',5'-dione.

As regards the (2R)-methyl derivative of sorbinil, this compound was first reported by K. Ueda et al. in Published U.K. Patent Application No. GB 2,080,304A, where it was called d-6-fluoro-2-methyl-spiro-[chroman-4,4'-imidazolidine]-2',5'-dione. It was prepared in a somewhat analogous manner to the original method of R. Sarges as outlined above, starting from p-fluorophenol and proceeding through the 6-fluoro-2-methyl-4-chromanone intermediate which was prepared by condensing p-fluorophenol with crotonic acid in the presence of polyphospheric acid. The resulting 6-fluoro-2-methyl-4-chromanone was then condensed with potassium cyanide and ammonium carbonate in the usual manner to ultimately afford dl-6-fluoro-2-methyl-spiro-[chroman-4,4'-imidazolidine]-2',5'-dione in the form of the desired diastereoisomer. Resolution of the latter dl-compound with an aqueous quinine methohydroxide solution then finally gave the desired d-6-fluoro-2-methyl-spiro-[chroman-4,4'-imidazolidine]-2',5'-dione, which is more properly called (4S)(2R)-6-fluoro-2-methyl-spiro-[chroman-4,4'-imidazolidine]-2',5'-dione in the present system of nomenclature.

SUMMARY OF THE INVENTION

In accordance with the present invention, there is now provided a new and especially useful process for preparing (4S)-6-fluoro-spiro-[chroman-4,4'-imidazolidine]-2',5'-dione (sorbinil) and its (2R)-methyl derivative by a unique series of reactions starting from the appropriate β-(4-fluorophenoxy)alkane halide compound as outlined in the accompanying reaction scheme. More particularly, the process of the invention comprises the steps of:

(1) amidoalkylation of the appropriate lower β-(4-fluorophenoxy)alkane halide compound of formula I, wherein R is hydrogen or methyl and X is halogen, with N-benzoyl-α-hydroxyglycine or N-(lower alkanoyl)-α-hydroxyglycine of the formula R'CONHCH(OH)-COOH, wherein R' is phenyl or alkyl having from one to four carbon atoms, in an acidic medium to form an intermediate 2-amidoalkylated derivative thereof represented by the formula II wherein R, R' and X are each as previously defined;

(2) dehydration and spiroalkylation of said intermediate amidoalkylated derivative of formula II by treatment with a dehydrating agent and a base to yield the desired spiroalkylated azlactone compound of formula III;

(3) contacting the 6-fluoro-spiro-[chroman-4,4'-2'-phenyloxazolidin-5'-one] or 6-fluoro-spiro-[chroman-4,4'-2'-(lower alkyl)oxazolidin-5'-one] compound of formula III with a mixture of a lower alkane hydrocarbon monocarboxylic acid having up to four carbon atoms and the appropriate hydrohalide acid at an elevated temperature to effect hydrolysis of said spiro-oxazolidin-5-one compound to the corresponding hydrohalide salt of the desired spiro-amino acid of formula IV;

(4) subjecting the 4-amino-6-fluorochroman-4-carboxylic acid or (2R)-4-amino-6-fluoro-2-methylchroman-4-carboxylic acid of formula IV in the form of a hydrohalide acid addition salt to esterification with thionyl chloride and the appropriate lower alkanol, followed by basification to form an intermediate racemic methyl or ethyl ester of formula V wherein R" is methyl or ethyl;

REACTION SCHEME

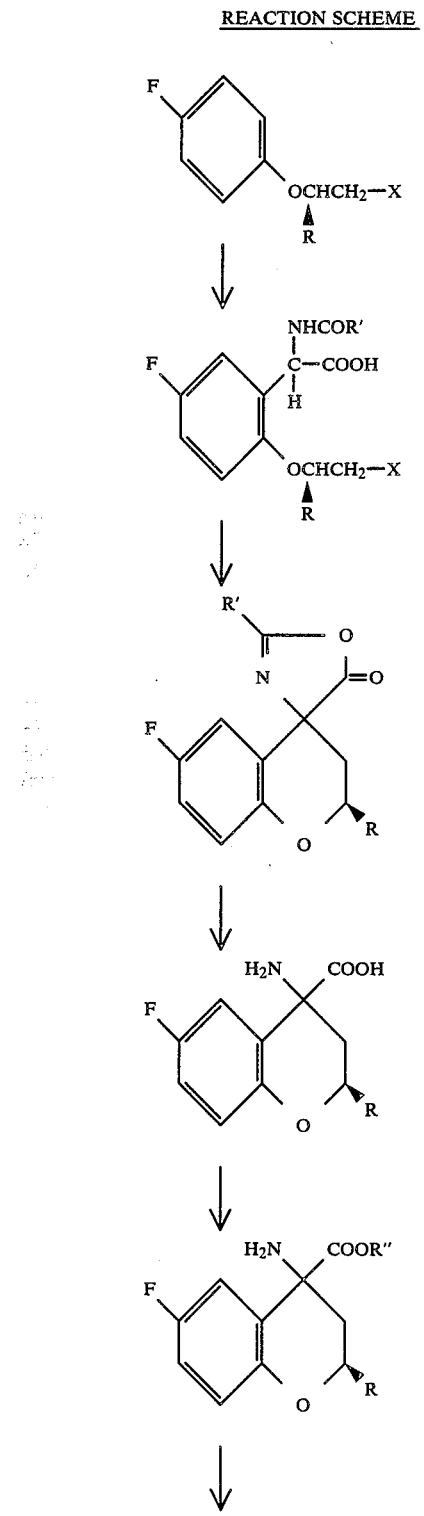

-continued
REACTION SCHEME

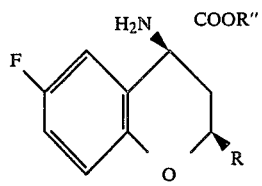

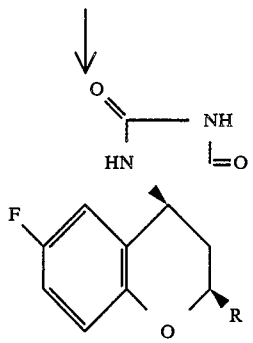

(5) resolution of said intermediate racemic ester of formula V by treatment with α-chymotrypsin to afford the desired (S)-methyl or (S)-ethyl ester of formula VI; and (6) contacting the (S)-methyl or (S)-ethyl ester of formula VI with an alkali metal cyanate in an acid medium to effect the conversion of said amino acid ester to the desired spiro-hydantoin ring compound of formula VII wherein R is hydrogen (i.e., sorbinil) or methyl [i.e., (2R)-methylsorbinil].

The invention also includes within its scope various novel intermediates used in the process, such as the spiro-oxazolidin-5-one compounds of formula III and the methyl and ethyl esters of formulas V-VI plus 4-amino-6-fluoro-(2R)-methylchroman-4-carboxylic acid (formula IV, R=CH₃). Typical and preferred spiro-oxadolidin-5-one compounds of formula III include those where R is hydrogen or methyl and R' is benzoyl or acetyl, such as, for example, 6-fluoro-spiro-[chroman-4,4'-2'-phenyloxazolidin-5'-one], 6-fluoro-spiro-[chroman-4,4'-2'-methyloxazolidin-5'-one] and 6-fluoro-(2R)-methyl-spiro-[chroman-4,4'-2'-phenyloxazolidin-5'one]. Typical and preferred methyl and ethyl esters of formula V-VI include those esters where R is hydrogen or methyl and R" is methyl or ethyl, such as, for example, methyl 4-amino-6-fluorochroman-4-carboxylate, (S)-methyl 4-amino-6-fluorochroman-4-carboxylate, methyl 4-amino-6-fluoro-(2R)-methylchroman-4-carboxylate and (4S)(2R)-methyl 4-amino-6-fluoro-2-methylchroman-4-carboxylate.

DETAILED DESCRIPTION OF THE INVENTION

In accordance with the process of the present invention for producing (4S)-6-fluoro-spiro-[chroman-4,4'-imidazolidine]-2',5'-dione (sorbinil) and its (2R)-methyl derivative (2-methylsorbinol) from readily available materials, the novel six-step method of synthesis is represented schematically by the reaction sequence hereinbefore set forth.

In the initial stage of the six-step method of synthesis, amidoalkylation of the appropriate lower β-(4-fluorophenoxy)alkane halide compound of the formula I is carried out by condensing the latter compound with N-benzoyl-α-hydroxyglycine or a N-(lower alkanoyl)-α-hydroxyglycine as previously defined in an acidic medium to give a 2-amidoalkylated derivative of the formula II. The acidic medium can be methanesulfonic acid, sulfuric acid and mixtures of sulfuric acid with acetic acid (e.g., 10–50% sulfuric acid in acetic acid). The preferred solvent is a mixture of 98% sulfuric acid in glacial acetic acid on a 50:50 by weight basis, particularly when considered from the point of view of cost consciousness, comparable yield and quality of product. The temperature for the reaction is not critical, e.g., from about 10° C. to about 40° C. and in practice, it is most convenient to carry out the reaction is the neighborhood of about room temperature (i.e., at ~20° C.), generally for a period of about two to about 48 hours. The molar ratio of formula I compound to N-substituted glycine is also not critical and can range from about 1.2:1.0 to about 1.0:1.5, respectively. Upon completion of the condensation step, the amidoalkylated derivative is readily isolated from the reaction mixture by conventional means, e.g., by pouring same onto ice or ice-water and filtering the thus precipitated product therefrom.

In the second stage of the six-step method of synthesis, dehydration and spiroalkylation of the amidoalkylated derivative of formula II to form the desired spiroalkylated azlactone compound of formula III is effected by treatment of the formula II compound with a dehydrating agent and a base in either a sequential or simultaneous manner. The dehydrating agent is preferably an acid anhydride derived from a lower alkane hydrocarbon monocarboxylic acid having up to four carbon atoms, such as acetic anhydride, propionic anhydride and the like, or it is a carbodiimide, such as dicyclohexylcarbodiimide, N,N'-carbonyl-diimidazole or 1-cyclohexyl-3-(2-morpholinoethyl)-carbodiimide metho-p-toluenesulfonate, etc., while the base employed is an inorganic or organic base and preferably a tertiary amine, such as triethylamine or pyridine, that serves to convert the intermediate azlactone (not isolated) to the desired spiroalkylated derivative via intramolecular alkylation (with concomitant removal of HX). The amidoalkylated derivative of formula II and the dehydrating agent are normally first contacted together in the presence of an aprotic solvent at a temperature ranging from about room temperature up to the reflux point of the reaction mixture, with a temperature that is in the range of about 20° C. up to about 100° C. being preferred. Preferred aprotic solvents include cyclic ethers such as dioxane and tetrahydrofuran, lower alkyl ketones such as acetone and methyl ethyl ketone, halogenated hydrocarbons such as methylene chloride and dichloroethane, lower aklkyl ($C_1$–$C_4$) esters of lower alkane hydrocarbon monocarboxylic acids like ethyl acetate, lower N,N-dialkyl ($C_1$–$C_4$) derivatives of amides derived from lower alkane hydrocarbon monocarboyxlic acids such as dimethylformamide, diethylformamide and dimethylacetamide, etc., and acetonitrile. The tertiary amine is then added to the reaction mixture without isolation of the intermediate azlactone (formed by reaction of formula II compound with the dehydrating agent), preferably employing at least about two equivalents of same in order to effect the spiroalkylation a temperature ranging from about 0° C. up to about 100° C. (and most preferably, from about 0° C. to about 70° C.). Reaction time is not critical and may vary from about 0.5 to about 24 hours. When a non-polar solvent such as tetrahydrofuran or methylene chloride is used as the initial solvent in the dehydration, it is desirable to employ a volume of lower N,N-dialkylalkanoamide solvent that is at least about equal to that of the tertiary amine reagent in order to enhance the overall rate of intramolecular alkylation. The molar ratio of formula II compound to dehydrating agent is not critical, but it is desirable to use an excess of the dehydrating agent with respect to the starting compound and preferably, at least about a 0.5 molar excess of said reagent. Upon completion of the dehydration-spiroalkylation reaction, the desired spiroalkylated azlactone compound of formula III is readily recovered from the reaction mixture by any number of conventional means, e.g., by first filtering to remove tertiary amine hydrohalide byproduct and then concentrating the resulting filtrate in vacuo, followed by further purification if necessary as hereinafter set forth in the examples of the experimental section of the instant specification.

In one preferred embodiment of the above described second-stage of the process of the present invention, an amidoalkylated derivative of the formula II wherein X is chlorine, bromine or iodine and the dehydrating agent, which is preferably the acid anhydride, are treated with two equivalents of tertiary amine reagent at room temperature. In this particular instance, the tertiary amine reagent, which is preferably triethylamine, catalyzes both the dehydration to the azlactone and the halogen displacement. In a mildly exothermic reaction, the desired product is formed in very high yield in less than an hour without heating and is subsequently readily isolated from the reaction mixture in a most facile manner by means of solvent extraction.

In another preferred embodiment of the second stage of the process, an amidoalkylated derivative of the formula II wherein X is bromine or iodine is treated with one equivalent of acid anhydride and two equivalents of an inorganic base, such as an alkali metal carbonate (e.g., potassium carbonate), in a lower alkyl ketone solvent, such as acetone, at room temperature. In this particular case, the reaction proceeds very cleanly over several hours without any heating being necessary. The desired spiroalkylated azlactone compound of formula II is then isolated from the reaction mixture by first removing solid byproducts therefrom via suction filtration and thereafter evaporating the aforesaid organic solvent from the system.

In this connection, it is to be noted that high yields of desired product (e.g., 75–95%) are achieved in both of the preferred embodiments under very mild operating conditions, a fact which is truly unusual and surprising for the formation of a quaternary carbon-carbon bond from a fairly inactive alkylating agent.

The third stage of the synthetic sequence of the present invention involves the hydrolysis of the 6-fluoro-spiro-[chroman-4,4'-2'-phenyloxazolidin-5'-one] or 6-fluoro-spiro-[chroman-4,4'-2'-(lower alkyl)oxazolidin-5'-one] of formula III to the corresponding 4-amino-6-fluorochroman-4-carboxylic acid or the (2R)-methyl derivative thereof of formula IV, wherein both acids are present in the form of their hydrohalide acid addition salts. This step is accomplished by contacting the formula III compound with a mixture of a lower alkane hydrocarbon monocarboxylic acid having up to four carbon atoms and the appropriate hydrohalide acid at an elevated temperature and preferably, by heating same at the reflux temperature of the reaction mixture. In this way, the hydrolysis of the formula III compound to the corresponding hydrohalide salt of the desired spiro-amino acid of formula IV is effected in a most facile manner. The preferred alkanoic acid is formic acid, while the preferred hydrohalide acid is concentrated hydrochloric acid. In general, the composition of the alkanoic acid/hydrohalide acid mixture will vary from about 3:1 to about 1:1, on a parts by volume basis, respectively, The reaction time required is not critical and will vary within a time period of from about two to about six hours at reflux, followed by a further period of stirring at room temperature if so desired. Upon completion of this step, the desired 4-amino-6-fluorochroman-4-carboxylic acid or the (2R)-methyl derivative thereof is readily isolated from the reaction mixture in the form of its hydrohalide salt by any number of conventional means, e.g., (1) by adding water and extracting with methylene chloride, followed by filtration and subsequent evaporation of the saved aqueous layer; or (2) by evaporating the reaction mixture first and them triturating the residue with acetone, etc.

The fourth stage in the overall method of synthesis of the present invention deals with the conversion of the 4-amino-6-fluorochroman-4-carboxylic acid or (2R)-4-amino-6-fluoro-2-methylchroman-4-carboxylic acid of formula IV (both as hydrohalide acid addition salts) to the corresponding methyl or ethyl esters of formula V (where R" is methyl or ethyl). This step is readily accomplished by any number of conventional esterification techniques and most preferably, by reacting the acid with thionyl chloride and the appropriate lower alkanol of choice in accordance with standard procedure [e.g., see L. F. Fieser and M. Fieser, "Reagents for Organic Synthesis", Vol. 1, John Wiley & Sons, Inc., New York, N.Y. (1967), p. 1160]. The acid is reacted with thionyl chloride in the selected alkanol medium (e.g., methanol or ethanol) at temperatures ranging from about −15° C. to about 10° C. to form the corresponding acid chloride in situ and the reaction mixture containing the latter intermediate is then heated at about 50° C. up to the reflux point of the mixture to convert the acid chloride to the desired ester. Although time is usually not a critical factor in this reaction, a period of at least about one hour is considered desirable but this will, or course, vary depending upon whether a higher or lower reaction temperature is employed. Upon completion of this step, the racemic ester so obtained is then easily isolated from the reaction mixture in a conventional manner, e.g., by first concentrating the mixture in vacuo to remove excess alkanol and other volatiles and thereafter triturating the residue with a nonpolar solvent such as diethyl ether. The spiro-amino acid ester (V) thus isolated is in the form of a hydrohalide acid addition salt nd requires further treatment with a base in a conventional manner to afford the corresponding free racemic spiro-amino acid methyl or ethyl ester (i.e., non-salt) of formula V. In this way, the hydrochloride acid addition salt of 4-amino-6-fluorochroman-4-carboxylic acid of formula IV is ultimately converted, via its acid chloride intermediate, to methyl 4-amino-6-fluorochroman-4-carboxylate of formula V. Alternatively, the hydrohalide acid addition salt of the formula V ester may be used as such in the next step of the process without any further treatment being necessary.

The fifth stage of the six-step method of synthesis of the present invention process involves the resolution of the intermediate racemic ester of formula V by treatment with α-chymotrypsin to afford the desired (S)-methyl or (S)-ethyl ester of formula VI. This particular step is readily accomplished by subjecting the racemic ester in a weakly acidic aqueous solution (pH of about 5) to the enzymatic action of the aforesaid protease enzyme, whereby the enzyme selectively hydrolyzes the (R)-ester to the corresponding acid while the (S)-ester remains largely intact. Although the use of α-chymotrypsin and related proteases to stereoselectively hydrolyze esters of α-amino acids is known [e.g., see J. Bryan Jones and J. F. Beck in "Techniques of Chemistry", Vol. X (Applications of Biochemical Systems in Organic Chemistry), Jones, Sih and Perlman, Editors, John Wiley & Sons, Inc., New York, N.Y., 1970, Chapter 4], the present step represents the first known instance of a spiro-amino acid ester having been resolved. The resolution is carried out in a dilute aqueous saline or alcohol (i.e., lower alkanol having up to four carbon atoms) solution at a pH maintained in the neighborhood of about pH 5.0 with the aid of pHstat control, using commercially available α-chymotrypsin as the resolving agent. The amount of α-chymotypsin employed as resolving agent is not critical as it need only be present in sufficient amount to catalyze the stereospecific hydrolysis, but it is most desirable to use at least about 5% by weight with respect to the starting racemic ester substrate in order to achieve optimum results. Although time and temperature are not critical factors in the resolution step, the stereoselective hydrolysis is normally conducted at ambient temperatures (e.g., 20°-25° C.) for a period of time until no further base untake is observed via the pHstat control. Upon completion of this step, the desired (S)-methyl or (S)-ethyl ester is readily isolated from the aqueous reaction mixture by first adjusting the pH to about 1.5-2.0 and then extracting with a water-immiscible organic solvent such as ethyl acetate, followed by a readjustment in pH of the saved aqueous portion to a pH value of about 10 and then further extraction with the aforesaid organic solvent to isolate the desired product. In this way, methyl 4-amino-6-fluorochroman-4-carboxylate of formula V (where R=H) is converted to (S)-methyl 4-amino-6-fluorochroman-4-carboxylate of formula VI which is the sorbinil precursor. In like manner, methyl 4-amino-6-fluoro-(2R)-methylchroman-4-carboxylate of formula V (where R=CH$_3$) is converted to (4S)(2R)-methyl 4-amino-6-fluoro-2-methylchroman-4-carboxylate of formula VI which is the precursor of (2R)-methylsorbinil.

The sixth and final stage of the multi-step process of the present invention involves converting the (S)-methyl 4-amino-6-fluorochroman-4-carboxylate or (4S)(2R)-methyl 4-amino-6-fluoro-2-methylchroman-4-carboxylate of formula VI to the corresponding spiro-hydantoin ring compound of formula VII (where R is respectively hydrogen or methyl). This step is readily accomplished by contacting the (S)-methyl or (S)-ethyl ester of formula VI with an alkali metal cyanate in an acid medium to effect the conversion of said amino acid ester to the desired spiro-hydantoin ring compound of formula VII wherein R is hydrogen (i.e., sorbinil) or methyl [i.e., (2R)-methylsorbinil]. The final conversion step is carried out by treating the formula VI ester with an excess of an alkali metal cyanate, such as sodium or potassium cyanate, in an acid medium that is preferably a lower alkane hydrocarbon monocarboxylic acid having up to four carbon atoms like glacial acetic acid at a temperature that is in the range of from about 20° C. up to about 120° C. until formation of the aforesaid formula VII spiro-hydantoin ring compound is substantially complete. Although time is not a critical factor in the overall conversion step, it is most often preferably to carry out the initial reaction for a period of least about 16 hours at room temperature (e.g., at about 20° C.) and then to complete the reaction at higher temperature (e.g. at about 100°–120° C.) for a period of about 2–5 hours. In this way, the resolved amino acid ester is first converted in situ to the corresponding 4-ureido derivative which is the primary reaction product at room temperature. The latter product is not isolated as such, but it is detected by thin layer chromatography (TLC) and high pressure liquid chromatography (HPLC) along with some hydantoin final product which slowly forms at room temperture, When the amino acid ester is completely converted to the ureido ester, heat treatment at the higher temperature will then allow ring closure to the spiro-hydantoin compound to take place (i.e., proceed to completion) in an accelerated manner. As previously indicated, the preferred alkali metal cyanate for the conversion is sodium or potassium cyanate and it need only be present in an equimolar amount with respect to the starting formula VI ester, but it is most desirable to employ an excess and preferably, at least a one mole excess. Upon completion of this step, the desired spiro-hydantoin final product is then easily isolated from the reaction mixture by conventional means, e.g., by first concentrating the reaction mixture in vacuo and then adding water to precipitate the product from the concentrate or else by treating the concentrate with a water-immiscible organic solvent such as ethyl acetate, followed by purification of the resulting organic solution and the subsequent removal of the organic solvent therefrom, etc. In this way, (S)-methyl 4-amino-6-fluorochroman-4-carboxylate of formula VI (where R=H) is converted via (S)-methyl 6-fluoro-4-ureidochroman-4-carboxylate to (4S)-6-fluoro-spiro-[chroman-4,4'-imidazolidine]-2',5'-dione of formula III which is sorbinil, while (4S)(2R)-methyl 4-amino-6-fluoro-2-methylchroman-4-carboxylate of formula VI (where R=CH$_3$) is converted via (4S)(2R)-methyl 6-fluoro-2-methyl-4-ureidochroman-4-carboxylate to (4S)(2R)-6-fluoro-2-methyl-spiro-[chroman-4,4'-imidazolidine]-2',5'-dione of formula VII which is (2R)-methylsorbinil.

Alternatively, the spiro-amino acid hydrohalide salt of formula IV can be converted to the desired spiro-hydantoin ring compound of formula VII in a known manner, involving a sequence of three reaction steps. More specifically, this alternate route involves treating the spiro-amino acid hydrohalide in water with an alkali metal cyanate to form the corresponding 4-ureido derivative, followed by resolution of the latter racemic intermediate as either the d-(+)-(1-phenylethyl)amine or the 1-(−)-ephedrine salt to give the desired diastereoisomeric salt which is then cyclized to the final product by heating in glacial acid. This method is also disclosed in Examples 32–37 of the present specification to illustrate the novel synthesis of (4S)(2R)-6-fluoro-2-methyl-spiro-[chroman-4,4'-imidazolidine]-2',5'-dione [i.e., (2R)-methylsorbinil] by this particular route. The intermediates involved in this particular alternate route to prepare (2R)-methylsorbinil, viz., 4-amino-6-fluoro-(2R)-methylchroman-4-carboxylic acid, 6-fluoro-(2R)-methyl-4-ureidochroman-4-carboxylic acid and the d-(+)-(1-phenylethyl)amine and 1-(−)-ephedrine salts of (4S)(2R)-6-fluoro-2-methyl-4-ureidochroman-4-carboxylic acid, are all novel compounds.

The ultimate starting materials required for use in the first step of the overall six-step method of synthesis of the process of the present invention, viz., the lower β-(4-fluorophenoxy)alkane halides of formula I, wherein R is hydrogen or methyl and X is halogen, and the N-acyl-α-hydroxyglycines of the formula R'(CONCH(OH)COOH, wherein R' is phenyl or alkyl having form one to four carbon atoms, are known compounds which are available commercially or by literature methods, or else they can easily be synthesized by those skilled in the art starting from common chemical reagents and using conventional methods of organic synthesis. Details in this regard are provided in preparations A–G, for the present purposes at hand, in the experimental section which immediately follows.

The advantages offered by the process of this invention as hereinbefore described are manifold: for instance, the use of highly toxic brucine together with high volumes of solvent is avoided; the total number of reaction steps is reduced from eight to six, thereby saving time and money; in the dehydration-spiroalkylation step of the present process, the yields obtained are of an extremely high order of magnitude; the overall process does not employ either acrylonitrile or potassium cyanide, both of which require special handling conditions; step (3) of the process allows for easy isolation of the desired spiro-amino acid of formula IV, which in turn, makes possible an enzymatic resolution of the corresponding methyl ester; and in the production of (2R)-methylsorbinil (formula VII, R=CH$_3$), the absolute configuration of the methyl substituent at the 2-position is clearly established since the process did not proceed through a racemate at C-2 but rather from the corresponding starting compound of structural formula I (which is ultimately derived from natural (S)-ethyl lactate).

PREPARATION A 2-(4'-Fluorophenoxy)ethyl bromide was prepared in one-step from p-fluorophenol and 1,2-dibromoethane according to the standard procedure described in the literature by C. S. Marvel et al. for phenoxyethyl bromide [see C. S. Marvel et al., "Organic Syntheses", Collective Vol. I, H. Gilman and A. H. Blatt, Editors, John Wiley & Sons, Inc., New York, N.Y., 1944, P. 436]. In this particular instance, p-fluorophenol was the starting material employed instead of phenol. The pure final product thus obtained, viz., 2-(4'-fluorophenoxy)ethyl bromide or 4-(2'-bromoethoxy)fluorobenzene (yield, 86%), was a colorless solid melting at 58°–60° C. and was further characterized by both nuclear magnetic resonance data and elemental analysis: NMR (CDCl$_3$) δ 7.1 (m, 4, aromatic C$\underline{H}$), 4.3 (t, 2, OC$\underline{H_2}$—), 3.7 (t, 2, BrC$\underline{H_2}$).

Anal. Calcd. for C$_8$H$_8$BrFO: C, 43.84; H, 3.65. Found: C, 44.03; H, 3.70.

PREPARATION B

The procedure described in Preparation A was repeated except that 1,2-dichloroethane was the reagent employed in place of 1,2-dibromoethane, using the same molar proportions as before. In this particular case, the corresponding final product obtained was 2-(4'-fluorophenoxy)ethyl chloride or 4-(2'-chloroethoxy)fluorobenzene (yield, 66%), a colorless oil characterized by the following nuclear magnetic resonance data: NMR (CDCl$_3$) δ 7.0 (m, 4), 4.2 (t, 2), 3.8 (t, 2).

PREPARATION C

To a solution of triphenylphosphine (139 g., 0.53 mole) in benzene (1.5 liters), there was added iodine (134.5 g., 0.53 mole) in six separate charges. The resultant mixture was next stirred for a period of two hours at the ambient temperature, followed by the addition of pyridine (79 ml., 0.98 mole) and then by the addition of a solution of 2-(4'-fluorophenoxy)ethanol (50 g., 0.32 mole), prepared as described in U.S. Pat. No. 4,341,905, dissolved in benzene (250 ml.). The resulting reaction mixture was then stirred for a period of 18 hours at room temperature ($\sim 20°$ C.) and thereafter diluted with methanol (200 ml.). At this point, the solids which had already formed were subsequently recovered by means of suction filtration and the filtrate thereafter successively washed with fresh separate portions of water (500 ml.), 10% aqueous sodium bisulfite (500 ml.), water (500 ml.), 1N hydrochloric acid ($2 \times 500$ ml.) and brine (200 ml.). Upon completion of this step, the benzene solvent was removed by means of evaporation under reduced pressure and hexanes were added to the concentrate to ultimately afford 78 g. (92%) of pure 2-(4'-fluorophenoxy)ethyl iodide or 4-(2'-iodoethoxy)fluorobenzene in the form of a white solid, m.p. 41°–43° C.; NMR (CDCl$_3$) $\delta$ 7.0 (m, 4), 4.2 (t, 2), 3.4 (t, 2).

PREPARATION D

To a stirred solution consisting of p-fluorophenol (7.5 g., 0.067 mole), (S)-ethyl lactate (7.9 g., 0.067 mole) and triphenylphosphine (18.75 g., 0.067 mole) all dissolved in tetrahydrofuran (100 ml.), there was added dropwise over a 15-minute period a solution consisting of diethylazodicarboxylate (12.5 g., 0.067 mole) dissolved in tetrahydrofuran (50 ml.). The resulting reaction solution was then stirred at room temperature ($\sim 20°$ C.) for a period of 18 hours. At this point, the tetrahydrofuran was removed by evaporation in vacuo and a mixture consisting of diethyl ether (150 ml.) and hexanes (150 ml.) was added to precipitate the solids. The latter were then removed by filtration, washed with hexanes and discarded. The resulting filtrate was thereafter washed with 1N aqueous sodium hydroxide ($2 \times 50$ ml.), water (50 ml.) and brine (50 ml.), followed by drying over anhydrous magnesium sulfate. After removal of the drying agent by means of filtration and the solvents by means of evaporation under reduced pressure, there was obtained an oil which was subjected to vacuum distillation to ultimately afford 10.2 g. (72%) of pure (R)-ethyl 2-(4'-fluorophenoxy)propionate, b.p. 90°–92° C./0.7 mm. Hg; $[\alpha]_D^{25°} +37.4°$ (c=2.148, CHCl$_3$); IR (CHCl$_3$) 1748 (C=O) cm$^{-1}$; NMR (CDCl$_3$) $\delta$ 7.0 (m, 4, aromatic CH), 4.8 (q, 1), 4.3 (q, 2), 1.6 (d, 3), 1.3 (t, 3).

Anal. Calcd. for C$_{11}$H$_{13}$FO$_3$: C, 62.26; H, 6.13. Found: C, 62.25; H, 6.22.

PREPARATION E (R)-Ethyl 2-(4'-fluorophenoxy)propionate (27.3 g., 0.129 mole), prepared as described in Preparation D, in dry tetrahydrofuran (100 ml.) was added dropwise to a stirred suspension of lithium aluminum hydride (3.8 g., 0.1 mole) in dry tetrahydrofuran (150 ml.). The resulting reaction mixture was then stirred for a period of three hours after completion of the addition. To the stirred mixture, there was then carefully added in a dropwise manner 10% aqueous tetrahydrofuran (30 ml.), saturated aqueous sodium sulfate solution (8 ml.) and finally solid sodium sulfate (5 g.). The spent reaction mixture was then stirred overnight ($\sim 16$ hours) at room temperature ($\sim 20°$ C.) to ensure completeness of reaction with respect to excess hydride. The resulting solids were then filtered and washed with hot tetrahydrofuran ($2 \times 75$ ml.). The combined filtrate and washings were thereafter evaporated under reduced pressure to remove the tetrahydrofuran and the residual oil thus obtained was subsequently dissolved in methylene chloride (150 ml.), followed by drying over anhydrous magnesium sulfate. After removal of the drying agent by means of filtration and the solvent by means of evaporation under reduced pressure, there was obtained an oil which was subjected to vacuum distillation to ultimately afford 20.3 g. (94%) of pure (R)-2-(4'-fluorophenoxy)propanol, b.p. 85°–95° C./0.6 mm. Hg; $[\alpha]_D^{25°} -33.0°$ (c=2.125, MeOH); NMR (CDCl$_3$) $\delta$ 7.1 (m, 4), 4.4 (m, 1), 3.8 (d, 2), 3.0 (broad s, OH), 1.3 (d, 3).

PREPARATION F

Bromine (19.8 g., 0.124 mole) was added dropwise to a solution of (R)-2-(4'-fluorophenoxy)propanol (20 g., 0.118 mole), prepared as described in Preparation E, and triphenylphosphine (32.4 g., 0.124 mole) dissolved in dimethylformamide (75 ml.), with the temperature being maintained below 25° C. by means of an ice water bath. The reaction mixture was then stirred at room temperature ($\sim 20°$ C.) for a period of 18 hours. The resulting solution was next diluted with ethyl acetate (500 ml.) and thereafter washed with water ($3 \times 200$ ml.), saturated aqueous sodium bicarbonate (150 ml.), water (150 ml.) and brine (75 ml.). The washed ethyl acetate solution was then dried over anhydrous magnesium sulfate, filtered and the resulting filtrate subsequently concentrated in vacuo to afford a slurry which was thereafter diluted with hexanes (250 ml.) and stirred for one-half hour. The precipitate which formed at this point was removed by means of filtration and the hexane filtrate was subsequently evaporated under reduced pressure to give an oil which was then subjected to vacuum distillation to ultimately afford 22.16 g. (80%) of pure (R)-1-bromo-2-(4'-fluorophenoxy)propane, b.p. 83°–85° C./0.15 mm. Hg; $[\alpha]_D^{25°} -10.2°$ (c=2.258, MeOH); IR (CHCl$_3$) 2956 (w), 2922 (w), 1726 (m), 1495 (m) cm$^{-1}$; NMR (CDCL$_3$) $\delta$ 7.1 (m, 4), 4.5 (m, 1), 3.5 (m, 2), 1.4 (d, 3); mass spectrum, (m/e) 233/231 (M$^+$), 112 (base peak, p-fluorophenol).

Anal. Calcd. for C$_9$H$_{10}$BrFO): C, 46.35; H, 4.29. Found: C, 46.36; H, 4.26.

PREPARATION G

Acetamide (6 g., 0.1 mole) and glyoxylic acid hydrate (9 g., 0.12 mole) were dissolved in acetone (100 ml.) and stirred at room temperature ($\sim 20°$ C.) overnight ($\sim 16$ hours). The acetone was then removed by means of evaporation under reduced pressure to yield a colorless oil which did not crystalize. The crude product (yield, 4.7 g.) consisted of a mixture of N-acetyl-$\alpha$-hydroxyglycine [pure monohydrate melts at 57° C., according to *Bull. Soc. Chim. Fr.* II, p. 248 (1978)] and acetamide according to NMR analysis, and was used as an intermediate without any further purification being necessary. NMR (DMSO-d$_6$) $\delta$ 8.6 (d, 1, N$\underline{H}$), 5.4 (d, 1, —C$\underline{H}$), 6.7 (H$_2$O), 2.8 (2s), 2.0 (s, 3).

EXAMPLE 1

4-(2'-Bromoethoxy)fluorobenzene (188.5 g., 0.86 mole), prepared as described in Preparation A, was added in a slow stream to cold methanesulfonic acid (620 ml.) with the aid of mechanical stirring. The resulting solution was then maintained at <15° C., while N-benzoyl-α-hydroxyglycine (156 g., 0.8 mole), available from the Aldrich Chemical Co., Inc. of Milwaukee, Wis. as α-hydroxyhippuric acid, was added thereto in several portions over a period of 20 minutes. The resulting reaction mixture was then allowed to warm slowly to room temperature (~20° C.) and thereafter stirred at the ambient temperature for a period of 40 hours. The viscous solution thus obtained was then poured over ice (~1.5 liters) with constant agitation to precipitate the crude product as a yellow solid. The latter material was subsequently collected by means of suction filtration, washed with water and then ethanol, and air-dried to constant weight to ultimately afford 310 g. (95%) of pure N-benzoyl-2-(2'-bromoethoxy)-5-fluorophenylglycine as a white powder, m.p. 208° C. (softens), 216°-219° C. (decomp.). Recrystallization from hot methanol then gave analytically pure material, m.p. 221° C. (softens), 232.5°-234° C. (decomp.); IR (KBr) 3568—2460 (broad), 1744 (s), 1720 (s), 1632 (s), 1605 (s) cm$^{-1}$; NMR (CDCl$_3$/DMSO-d$_6$) δ 8.9 (d, 1, N$\underline{H}$), 8.0 (m, 2, o-benzoyl C$\underline{H}$), 7.55 (m, 3, m, p-benzoyl C$\underline{H}$), 7.2 (m, 3, p-fluorophenoxy C$\underline{H}$), 6.1 [d, 1, —C$\underline{H}$ (NHCO-phenyl)-COOH], 4.4 (t, 2, —C$\underline{H_2}$O—), 3.8 (t, 2 —C$\underline{H_2}$Br); mass spectrum, (m/e) 395.9 (M$^+$), 351 (M$^+$—COOH).

Anal. Calcd. for C$_{17}$H$_{16}$NBrFO$_4$: C, 51.56; H, 3.82; N, 3.54. Found: C, 52.42; H, 3.96; N, 3.64.

EXAMPLE 2

α-Hydroxyhippuric acid (1.3 kg., 6.6 moles) was added in several portions over a 25-minute period to 98% sulfuric acid (1.6 liters) with the aid of ice bath cooling to maintain the temperature below 32° C. The resulting solution was then stirred while 4-(2'-bromoethoxy)fluorobenzene (1.42 kg., 6.5 moles) dissolved in glacial acetic acid (1.6 liters) was slowly added thereto in a continuous stream over a 45-minute period, with external cooling being maintained to keep the reaction temperature in the 30°-36° C. range. After the addition step was complete, the reaction mixture was stirred at 30° C. for a period of 1.5 hours. At this point, ice (1.5 kg.) was added to the stirred reaction solution followed by the addition thereto of water chilled to 10° C. (12.5 liters), with external cooling being maintained to regulate the temperature to value ≦25° C. The precipitated product obtained in this manner was thereafter granulated for a period of one hour. The latter material was subsequently collected by means of suction filtration, washed well with water (4 liters) and air-dried to constant weight to ultimately afford 2.3 kg. (90%) of pure N-benzoyl-2-(2'-bromoethoxy)-5-fluorophenylglycine which was identical in every respect with the product of Example 1.

EXAMPLE 3

The procedure described in Example 1 was repeated except that 4-(2'-chloroethoxy)fluorobenzene (prepared as described in Preparation B) was the starting material employed in place of 4-(2'-bromoethoxy)fluorobenzene, using the same molar proportions as before. In this particular case, the corresponding final product obtained was N-benzoyl-2-(2'-chloroethoxy)-5-fluorophenylglycine (yield, 92%), m.p. 221°-224° C.; NMR (DMSO-d$_6$) δ 9.0 (d, J=7Hz), 8.1 (M, 2), 7.8-7.1 (m, 6), 6.2 (d, J=7Hz), 4.4 (m, 2), 4.0 (m, 2 ), mass spectrum, (m/e) 352/354 (M$^+$, Cl isotope), 105 (base peak, C$_6$H$_5$C≡O$^+$).

Anal. Calcd. for C$_{17}$H$_{15}$FClNO$_4$: C, 58.09; H, 4.31; N, 3.99. Found: C, 57.56; H, 4.38; N, 3.81.

EXAMPLE 4

The procedure described in Example 1 was repeated except that 4-(2'-iodoethoxy)fluorobenzene (prepared as described in Preparation C) was the starting material employed in place of 4-(2'-bromoethoxy)fluorobenzene, using the same molar proportions as before. In this particular case, the corresponding final product obtained was N-benzoyl-2-(2'-iodoethoxy)-5-fluorophenylglycine (yield, 88%), m.p. 210°-220° C. (darkens), 229°-232° C. (decomp.); IR (KBr) 3432 (s), 1745 (s), 1632 (s), 1576 (s), 1530 (s), 1498 (s) cm$^{-1}$; NMR (DMSO-d$_6$) δ 9.05 (d, 1) 8.2-7.0 (m, 8), 6.3 (d, 1), 4.4 (t, 2), 3.6 (t, 2); mass spectrum, (m/e) 444 (M$^+$), 398 (M$^+$—HCO$_2$), 105 (base peak, C$_6$H$_5$C≡O$^+$).

Anal. Calcd. for C$_{17}$H$_{15}$FINO$_4$: C, 46.09; H, 3.42; N, 3.16. Found: C, 46.07; H, 3.52; N, 3.07.

EXAMPLE 5

4-(2'-Bromoethoxy)fluorobenzene (4.35 g., 0.02 mole) and N-acetyl-α-hydroxyglycine (4.7 g., 0.035 mole based on 100% material), prepared as described in Preparation G, were stirred together with cooling while methanesulfonic acid (13 ml.) was added dropwise thereto over a period of five minutes. The resulting reaction mixture was then stirred at room temperature (~20° C.) for a period of 18 hours. At this point, the spent reaction mixture was poured into ice water and the precipitated product was subsequently collected by means of suction filtration and dried in vacuo to constant weight to ultimately afford 3.8 g. (56%) of pure N-acetyl-2-(2'-bromoethoxy)-5-fluorophenylglycine, m.p. 170°-178° C. (decomp.); IR (KRr) 3367 (s), 1731 (s), 1595 (s), 1536 (s), 1502 (s) cm$^{-1}$; NMR (DMSO-d$_6$) δ 8.6 (d, 1), 7.3 (m, 3), 5.9 (d, 1), 5.5-4.5 (broad, O$\underline{H}$), 4.5 (t, 2), 3.9 (m, 2), 2.0 (s, 3); mass spectrum, (m/e) 334/336 (M$^+$, Br).

EXAMPLE 6

The procedure described in Example 1 was repeated except that (R)-1-bromo-2-(4'-fluorophenoxy)propane (prepared as described in Preparation F) was the starting material employed in place of 4-(2'-bromoethoxy)-fluorobenzene, using the same molar proportions as before. In this particular case, the corresponding final product obtained was N-benzoyl-2-[(2'R)-1'-bromopropoxy]-5-fluoro-(R)(S)-phenylglycine (yield, 83%), m.p. 203°-210° C.; NMR (DMSO-d$_6$) δ 8.9 (t, 1), 8.2-7.1 (m, 8), 6.1 (d, 2), 4.7 (m, 1), 3.7 (d, 2), 1.3 (dd, 3).

Anal. Calcd. for C$_{18}$H$_{17}$FBrNO$_4$: C, 52.73; H, 4.18; N, 3.42. Found: C, 52.78; H, 4.22; N, 3.40.

EXAMPLE 7

The procedure described in Example 5 is repeated except that (R)-1-bromo-2-fluorophenoxy)propane (prepared as described in Preparation F) is the starting material employed instead of 4-(2'-bromoethoxy)fluorobenzene, using the same molar proportions as before. In this particular case, the corresponding final product obtained is N-acetyl-2-[(2'R)-1'-brommopropoxy]-5-fluoro-(R)(S)-phenylglycine.

EXAMPLE 8

N-Benzoyl-2-(2'-bromoethoxy)-5-fluorophenylglycine (50 g., 0.126 mole), prepared as described in Example 1, and acetic anhydride (25 g., 0.252 mole) were heated at reflux in tetrahydrofuran (250 ml.) to cause conversion to 4'-[2-(2-brommoethoxy)-5-fluorophenyl]-2'-phenyloxazolidin-5'-one. The reaction mixture was then cooled to 5° C. and a solution of triethylamine (25.5 g., 0.252 mole) in dimethylformamide (35 ml.) was added dropwise thereto. The resulting reaction mixture was then slowly warmed to room temperature (~20° C.) and stirred at the ambient temperature for a period of 18 hours. At this point, some precipitated triethylamine hydrobromide was removed by means of filtration and washed with tetrahydrofuran. The tetrahydrofuran and excess acetic anhydride were then removed by means of evaporation under reduced pressure, and the residual oil so obtained was subsequently taken up in ethyl acetate. The latter organic solution was then successively washed with water (twice), 5% aqueous sodium bicarbonate, 1N hydrochloric acid and saturated aqueous sodium chloride (brine), followed by drying over anhydrous magnesium sulfate. After removal of the drying agent by means of filtration and the solvent by means of evaporation under reduced pressure, there was finally obtained an orange oil in 75-95% yield as the residual product. This proved to be essentially pure 6-fluoro-spiro-[chroman-4,4'-2'-phenyloxazolidin-5'-one] of suitable quality for further reaction, IR ($CH_2Cl_2$) 1825 (s), 1819 (s), 1651 (s), 1492 (s) cm$^{-1}$; NMR ($CDCl_3$) δ 8.2 (m, d, aromatic C$\underline{H}$), 7.8 (m, 3, m, p-benzoyl C$\underline{H}$), 7.0 (m, 2) and 6.7 (m, 1, fluoroaromatic C$\underline{H}$), 4.5 (m, 2, —C$\underline{H}_2$O—), 2.3 (t, 2, —C$\underline{H}_2$—C$\underline{H}_2$); mass spectrum, (m/e) 297 (M+), 269 (M+—$CO_2$), 253 (M+—$CO_2$), 104.9 (base peak, $C_6H_5C\equiv O^+$).

EXAMPLE 9

A suspension of N-benzoyl-2-(2'-bromoethoxy)-5-fluorophenylglycine (2.363 kg., 6.0 moles) in dry dimethylformamide (1.8 liters) was treated with acetic anhydride (1.218 kg., 11.9 moles) in one portion. The resulting mixture was then cooled to 20° C. in a water bath kept at 10° C., while triethylamine (1.218 kg., 12 moles) was slowly added thereto over a period of 40 minutes. During the course of the addition, the reaction mixture became a solution and shortly thereafter (toward the end of the addition) incipient crystallization of triethylamine hydrobromide took place. During this time, the temperature of the reaction mixture rose slowly from 20° C. to 55° C. and then fell to 40° C. upon completion of this step. At this point, the reaction mixture was warmed to 50° C. for a period of 30 minutes in order to ensure completeness of reaction. The spent mixture so obtained was then cooled to 25° C. and toluene (6 liters) and water (6 liters) were added thereto, which, in turn, afforded a separation into two layers. The separated aqueous layer was next extracted again with toluene (3 liters), and the combined toluene layers were subsequently washed with water (3×3 liters) and thereafter dried over anhydrous magnesium sulfate (2 lbs.). After removal of the drying agent by means of filtration and the volatiles by means of evaporation under reduced pressure, there was finally obtained the desired product, viz., 6-fluoro-spiro-[chroman-4,4'-2'-phenyloxazolidin-5'-one], as an amber oil concentrate (1.866 kg.).

EXAMPLE 10

The procedure described in Example 9 is repeated except that N-benzoyl-2-(2'-chloroethoxy)-5-fluorophenylglycine (prepared as described in Example 3) is the starting material employed instead of N-benzoyl-2-(2'-bromoethoxy)-5-fluorophenylglycine, using the same molar proportions as before. In this particular case, the corresponding final product obtained is 6-fluoro-spiro-[chroman-4,4'-2'-phenyloxazolidin-5'-one], identical in every respect with the product of Example 8.

EXAMPLE 11

The procedure described in Example 9 is repeated except that N-benzoyl-2-(2'-iodoethoxy)-5-fluorophenylglycine (prepared as described in Example 4) is the starting material employed instead of N-benzoyl-2-(2'-bromoethoxy)-5-fluorophenylglycine, using the same molar proportions as before. In this particular case, the corresponding final product obtained is 6-fluoro-spiro-[chroman-4,4'-2'-phenyloxazolidin-5'-one], identical in every respect with the product of Example 8.

EXAMPLE 12

N-Acetyl-2-(2'-bromoethoxy)-5-fluorophenylglycine (1.5 g., 0.0045 mole), prepared as described in Example 5, was dissolved in dimethylformamide (5 ml.) containing acetic anhydride (0.9 g., 0.009 mole). The resulting organic solution was then stirred at room temperature (~20° C.), while triethylamine (0.9 g., 0.009 mole) was added quickly thereto in one portion. The reaction mixture thus obtained was next stirred at room temperature for a period of 15 minutes and thereafter stirred at 60° C. for a period of one hour. The spent reaction mixture was then cooled and diluted with ethyl acetate (25 ml.), and the latter solution was subsequently washed with successive portions of water (2×25 ml.), 1N hydrochloric acid (1×15 ml.), water (1×10 ml.) and brine (10 ml.). The washed extract was then dried over anhydrous magnesium sulfate and filtered, and the resulting filtrate was subsequently concentrated in vacuo to give an oil. The latter product proved to be pure 6-fluoro-spiro-[chroman-4,4'-2'-methyloxazolidin-5'-one] in 1.0 g. (100%) yield, NMR ($CDCl_3$) δ 7.1 (m, 2), 6.7 (m, 1), 4.4 (m, 2), 2.4–1.8 (m, 5).

The above product was then further characterized by heating in 3N aqueous sodium hydroxide (6 ml.) at the reflux temperature for a period of two hours, followed by cooling and acidification to ultimately give 0.7 g. of N-acetyl-4-amino-6-fluorochroman-4-carboxylic acid (60% yield based on the bromoethoxy starting material), m.p. 229°–234° C. (decomp.); mass spectrum, (m/e) 253 (M+), 209 (M+—$CO_2$).

EXAMPLE 13

N-Benzoyl-2-[(2'R)-1'-bromopropoxy]-5-fluoro-(R)(S)-phenylglycine (25 g., 0.061 mole), prepared as described in Example 6, and potassium carbonate (16.85 g., 0.122 mole) were suspended in acetone (100 ml.) and treated with acetic anhydride (9.2 g., 0.09 mole) at room temperature (~20° C.). The resulting reaction mixture was then stirred at the ambient temperature for a period of 24 hours, during which time precipitation of salts (i.e., potassium bromide) occurred. The spent reaction mixture was then filtered and the resulting filtrate subsequently concentrated in vacuo to afford an orange oil (yield, 17 g.) which proved to be essentially pure 6-fluoro-(2R)-methyl-spiro-[chroman-4,4'-2'-phenyloxazolidin-5'-one], NMR (CDCl$_3$) δ 8.2 (m, 2), 7.7 (m, 3), 7.1 (m, 2), 6.7 (m, 1), 4.7 (m, 1), 2.4–2.0 (m, 2), 1.5 (m, 3).

EXAMPLE 14

The procedure described in Example 13 is repeated except that N-acetyl-2-[(2'R)-1'-bromopropoxy]-5-fluoro-(R)(S)-phenylglycine prepared as described in Example 7) is the starting material employed instead of N-benzoyl-2-[(2'R)-1'-bromopropoxy]-5-fluoro-(R)(S)-phenylglycine, using the same molar proportions as before. In this particular case, the corresponding final product obtained is 6-fluoro-(2R)-methyl-spiro-[chroman-4,4'-2'-methyloxazolidin-5'-one].

EXAMPLE 15

6-Fluoro-spiro-[chroman-4,4'-2'-phenyloxazolidin-5'-one] (37.4 g., 0.126 mole), prepared as described in Example 8, was dissolved in formic acid (125 ml.) and concentrated (36%) hydrochloric acid (100 ml.) was added to the acidic solution. The resulting reaction mixture was then heated at the reflux temperature for a period of three hours and thereafter stirred at room temperature (~20° C.) overnight (~16 hours). At this point, water (250 ml.) was added to the spent reaction mixture which was then extracted twice with methylene chloride and filtered. The resulting aqueous filtrate was thereafter evaporated in vacuo to afford crude 4-amino-6-fluorochroman-4-carboxylic acid in the form of the hydrochloride salt. The latter salt, which contained water, was then dissolved in isopropanol and the alcoholic solution concentrated in vacuo to azeotrope most of the water. This step was repeated to ensure completeness for the present purposes at hand, and the resulting residual oil was thereafter taken up in acetone and treated with diethyl ether to precipitate the desired salt from solution. The precipitated product was subsequently collected by means of suction filtration, washed with diethyl ether and dried in vacuo to constant weight to ultimately afford pure 4-amino-6-fluorochroman-4-carboxylic acid hydrochloride in 60–85% yield, m.p. 253°–254° C. (decomp.); IR (KBr) 3650–2300 (broad), 1731 (s, COOH), 1497 (s) cm$^{-1}$.

EXAMPLE 16

N-Acetyl-4-amino-6-fluorochroman-4-carboxylic acid (4 g., 0.016 mole), prepared as described in Example 12, was heated in a mixture of formic acid (15 ml.) and concentrated hydrochloric acid (10 ml.) at the reflux temperature for a period of six hours. The volatiles were then stripped from the reaction mixture by means of evaporation under reduced pressure, and the wet solid which resulted was subsequently triturated with acetone and thereafter collected by means of suction filtration and air-dried to constant weight. In this manner, there were ultimately obtained 3.5 g. (88%) of pure 4-amino-6-fluorochroman-4-carboxylic acid hydrochloride, m.p. 266°–267° C. (decomp.). The pure product was further characterized by means of infrared absorption spectra (IR), thin layer chromatography studies (TLC) and high pressure liquid chromatography (HPLC), as well as elemental analysis.

Anal. Calcd. for C$_{10}$H$_{10}$FNO$_3$.HCl: C, 48.50; H, 4.48; N, 5.66. Found: C, 48.37; H, 4.51; N, 5.54.

EXAMPLE 17

The procedure described in Example 15 is repeated except that 6-fluoro-spiro-[chroman-4,4'-2'-methyloxazolidin-5'-one] (prepared as described in Example 12) is the starting material employed instead of 6-fluoro-spiro-[chroman-4,4'-2'-phenyloxazolidin-5'-one], using the same molar proportions as before. In this particular case, the corresponding final product obtained is 4-amino-6-fluorochroman-4-carboxylic acid hydrochloride, identical in every respect with the product of Example 15.

EXAMPLE 18

6-Fluoro-(2R)-methyl-spiro-[chroman-4,4'-2'-phenyloxazolidin-5'-one] (3.0 g., 0.0096 mole), prepared as described in Example 13, was heated in a mixture of formic acid (10 ml.) and concentrated hydrochloric acid (10 ml.) at the reflux temperature for a period of six hours. The resulting reaction mixture was then cooled to room temperature (~20° C.) and subsequently concentrated in vacuo to afford a solid mass. The latter material, viz., crude 4-amino-6-fluoro-(2R)-methylchroman-4-carboxylic acid in the form of the hydrochloride salt and benzoic acid, was then taken up in water and extracted twice with diethyl ether. The resulting aqueous layer was then saved and subsequently adjusted to pH 5 with 1N aqueous sodium hydroxide, followed by evaporation under reduced pressure to give an oil. The latter was then dissolved in isopropanol, and the resulting alcoholic solution was subsequently concentrated in vacuo to near dryness to yield a residue. Treatment of the latter material with acetone then gave the desired product in the form of a crystalline solid. In this manner, there were ultimately obtained 1.0 g. (46%) of pure 4-amino-6-fluoro-(2R)-methylchroman-4-carboxylic acid, m.p. 229°–233° C. (decomp.); IR (KBr) 1624 (s), 1564 (s), 1489 (s), 1444 (m) cm$^{-1}$; NMR (250 MHz, D$_2$O) δ 7.25–6.9 (m, 3), 4.9 (HOD), 4.35 (m, 0.5, C$\underline{H}$, one diastereoisomer, 2.7–2.28 (m, 2), 1.5 and 1.48 (d$\underline{d}$, 3).

EXAMPLE 19

The procedure described in Example 18 is repeated except that 6-fluoro-(2R)-methyl-spiro-[chroman-4,4'-2'-methyloxazolidin-5'-one] (prepared as described in Example 14) is the starting material employed instead of 6-fluoro-(2R)-methyl-spiro-[chroman-4,4'-2'-phenyloxazolidin-5'-one], using the same molar proportions as before. In this particular case, the corresponding final product obtained is 4-amino-6-fluoro-(2R)-methylchroman-4-carboxylic acid (first isolated as the crude hydrocholoride salt), identical in every respect with the product of Example 18.

EXAMPLE 20

To well-stirred, cold methanol (75 ml.) maintained at −10° C. to 0° C., there was added thionyl chloride (19ml.) in a dropwise manner with continued agitation. 4-Amino-6-fluorochroman-4-carboxylic acid hydrochloride (15 g., 0.071 mole), prepared as described in Example 15, was then added as a solid and the resulting mixture was slowly warmed to room temperature (~20° C.). After stirring at this point for a period of four hours, the mixture so obtained was heated at the reflux point for a period of approximately 16 hours (i.e., overnight). The resulting reaction mixture was then cooled and the methanol removed therefrom by means of evaporation under reduced pressure to afford a thick liquid as residue. The latter material soon solidified and was slurried in diethyl ether prior to being collected by means of suction filtration. In this manner, there were ultimately obtained 18 g. (97%) of pure methyl 4-amino-6-fluorochroman-4-carboxylate hydrochloride, m.p. 200°-202° C. (decomp.). The solid spiro-amino acid methyl ester hydrochloride prepared above (18 g.) was then dissolved in water (60 ml.) with ethyl acetate and cooled in an ice water bath, while the pH of the aqueous layer was adjusted to pH 10. The two lyers were then separated and the aqueous layer was subsequently extracted twice with ethyl acetate. The combined organic layers were thereafter washed with saturated aqueous sodium chloride solution (brine), dried over anhydrous magnesium sulfate and filtered. After removal of the drying agent by means of filtration and the solvent by means of evaporation under reduced pressure, there was obtained a residual oil which soon crystallized. The resulting solid mass was then broken up in hexanes and subsequently collected by means of suction filtration to ultimately afford 11.71 g. (73%) of pure methyl 4-amino-6-fluoro-chroman-4-carboxylate in the form of a white solid, m.p. 64–65.5° C.; NMR (CDCl$_3$) δ 7.0 (m, 3, aromatic C$\underline{H}$) 4.4 (m, 2, —OC$\underline{H}_2$—), 3.8 (s, 3, —OC$\underline{H}_3$), 2.8–2.3 (m, 1, C$\underline{H}_2$), 2.1–1.7 (m and s, 3, —N$\underline{H}_2$ and C$\underline{H}_2$).

Anal. Calcd. for C$_{11}$H$_{12}$FNO$_3$: C, 58.66; H, 5.37; N, 6.22. Found: C, 58.48; H, 5.24; N, 6.08.

EXAMPLE 21

The procedure described in Example 20 is repeated except that ethanol is the reagent of choice employed instead of methanol, using the same molar proportions as before. In the particular case, the corresponding final product obtained is ethyl 4-amino-6-fluorochroman-4-carboxylate.

EXAMPLE 22

6-Fluoro-(2R)-methyl-spiro-[chroman-4,4'-2'-phenyloxazolidin-5'-one] (18.6 g., 0.06 mole), prepared as described in Example 13, was heated in mixture of formic acid (75 ml.) and concentrated hydrochloric acid (30 ml.) at the reflux temperature for a period of 16 hours. The resulting reaction mixture was then cooled to room temperature (~20° C.) and concentrated in vacuo to a volume of 20 ml. The latter concentrate was then diluted with water (50 ml.) and twice extracted with diethyl ether. The resulting aqueous layer was then saved and subsequently concentrated in vacuo to afford a solid. The latter material was thereafter azeotroped (twice) to remove water via evaporation of isopropanol and the purified material was subsequently dissolved in methanol. The resulting methanolic solution containing 4-amino-6-fluoro-(2R)-methylchroman-4-carboxylic acid hydrochloride was then added with constant agitation to a cold solution consisting of thionyl chloride (7 ml.) dissolved in methanol (150 ml. ). The resulting reaction mixture was then refluxed for a period of 18 hours and cooled to room temperature. At this point, the methanol was removed by means of evaporation under reduced pressure and the residual brown oil was subsequently dissolved in water (100 ml.) and extracted twice with ethyl acetate. The separated aqueous layer was then cooled and saved, and the pH of same was subsequently adjusted to pH 10 with 6N aqueous sodium hydroxide prior to further extraction with ethyl acetate (twice). The organic layers were then combined, washed with brine and dried over anhydrous magnesium sulfate. After removal of the drying agent by means of filtration and the solvent by means of evaporation under reduced pressure, there were obtained 7.28 g. (51%) of pure methyl 4-amino-6-fluoro-(2R)-methylchroman-4-carboxylate in the form of a light brown oil, IR (CHCl$_3$) 2947 (w), 1732 (s), 1484 (s), 1425 (m) cm$^{-1}$; NMR (CDCl$_3$) δ 7.5–6.8 (m, 3), 4.6 (m, 1), 3.8 (s, 3), 2.65–1.65 (m, 4, C$\underline{H}_2$, —N$\underline{H}_2$), 1.5 and 1.4 (dd, 3); mass spectrum, (m/e) 239 (M+), 180 (M+—COOCH$_3$, base peak).

The methyl ester obtained above was a mixture of two diastereoisomers. These isomers were separated through medium pressure liquid chromatography over silica gel by elution with 1% methanol in chloroform. The desired (4S)(2R)-methyl 4-amino-6-fluoro-2-methylchroman-4-carboxylate was the second eluting ester and was isolated as a light yellow oil, $[\alpha]_D^{25°}$ +132.2° (c=0.696, CHCl$_3$); NMR (CDCl$_3$) δ 7.4–6.8 (m, 3), 4.8–4.2 (m, 1), 3.8 (s, 3), 2.5/2.3 (dd, 1), 2.1 (s, 2, —N$\underline{H}_2$), 1.8 (d, 1), 1.35 (d, 3).

EXAMPLE 23

The procedure described in Example 22 is repeated except that ethanol is employed in lieu of methanol in the esterification step, using the same molar proportions as before. In this particular case, the corresponding final product obtained is ethyl 4-amino-6-fluoro-(2R)-methylchroman-4-carboxylate.

EXAMPLE 24

Methyl 4-amino-6-fluorochroman-4-carboxylate (11.5 g., 0.051 mole), the racemic spiro-amino acid methyl ester prepared in Example 20, was dissolved in 0.125M aqueous sodium chloride solution (100 ml.) at pH 5 by the addition of 6N hydrochoric acid. α-Chymotrypsin (750 mg.), available from the Sigma Chemical Company of St. Louis, MO., was then added to the mixture with stirring at room temperature (~20° C.). After an initial induction period of several hours, hydrolysis commenced as evidenced by the uptake of 0.5N aqueous sodium hydroxide from a pHstat to maintain the pH of the reaction solution at pH 5.1. The reaction was then continued until the uptake of base ceased. The reaction mixture was then acidified with 6N hydrochloric acid to pH 2 and activated carbon (1 g.) was added. After stirring for two hours, supercel (0.5 g.) was added and stirring was continued for another three hours. The spent reaction mixture was then filtered through supercel and extracted with ethyl acetate. The acqueous layer so obtained was adjusted to pH 10 with 6N aqueous sodium hydroxide and thereafter extracted with ethyl acetate (three times). The combined organic layers were then washed with brine and dried over anhydrous magnesium sulfate. After removal of the drying agent by means of filtration and the solvent by means of evaporation under reduced pressure, there were obtained 4.17 g. of pure (S)-methyl 4-amino-6-fluorochroman-4-carboxylate (73% yield based on available enantiomer) in the form of a colorless oil, $[\alpha]_D^{25°}$ +51.2° (c=0.64, CHCl$_3$); NMR (CDCL$_3$) identical with the racemic amino acid ester.

EXAMPLE 25

The procedure described in Example 24 is repeated except that ethyl 4-amino-6-fluorochroman-4-carboxylate (prepared as described in Example 21) is the starting material employed instead of methyl 4-amino-6-fluorochroman-4-carboxylate, using the same molar proportions as before. In this particular case, the corresponding final product obtained is (S)-ethyl 4-amino-6-fluorochroman-4-carboxylate.

EXAMPLE 26

The diastereomeric ester mixture prepared in Example 22, viz., methyl 4-amino-6-fluoro-(2R)-methyl-chroman-4-carboxylate (2 g.), was dissolved in methanol (3 ml.) and one equivalent of 1N hydrochloric acid (~6 ml.) was added. The resulting solution was then diluted to 50 ml. with distilled water and the pH was subsequently adjusted to pH 5.0 with 0.5N aqueous sodium hydroxide. α-Chymotrypsin (0.2 g.) was then added and the reaction mixture stirred with pHstat control until the uptake of base ceased (one-half equivalent was required). The pH of the resulting mixture was then lowered to pH 1.5 with 6N hydrochloric acid, followed by the addition of activated carbon (0.5 g.) and supercel (0.5 g.). After stirring for two hours, the spent mixture was filtered and thereafter extracted with ethyl acetate. The resulting aqueous layer was then cooled to 10° C. and the pH subsequently adjusted to pH 10 with 6N aqueous sodium hydroxide, followed by extraction with ethyl acetate (3×25 ml.). The organic layers were then combined and subsequently washed with brine and dried over anhydrous magnesium sulfate. After removal of the drying agent by means of filtration and the solvent by means of evaporation under reduced pressure, there was obtained 0.75 g. (38%) of pure (4S)(2R)-methyl 4-amino-6-fluoro-2-methylchroman-4-carboxylate, which was identical in every respect with the corresponding final product of Example 22.

EXAMPLE 27

The procedure described in Example 26 is repeated except that ethyl 4-amino-6-fluoro-(2R)-methylchroman-4-carboxylate (prepared as described in Example 23) is the starting material employed instead of methyl 4-amino-6-fluoro-(2R)-methylchroman-4-carboxylate, using the same molar proportions as before. In this particular case, the corresponding final product obtained is (4S)(2R)-ethyl 4-amino-6-fluoro-2-methylchroman-4-carboxylate.

EXAMPLE 28

(S)-Methyl 4-amino-6-fluorochroman-4-carboxylate (4.17 g., 0.0185 mole), prepared as described in Example 24, was stirred with sodium cyanate (2.55 g., 0.0392 mole) in glacial acetic acid (40 ml.) at room temperature (~20° C.) for a period of 24 hours (complete solution occurred after two hours). Upon completion of this step, the reaction mixture was heated at 90° C. for a period of three hours and thereafter concentrated in vacuo to a volume of 20 ml. At this point, warm water (60 ml.) was added to the spent mixture, which was then cooled and filtered. The crude product obtained as the filter cake was then recrystallized from isopropanol to afford 2.58 g. (61%) of pure (4S) -6-fluoro-spiro-[chroman-4,4'-imidazolidine]-2',5'-dione which is sorbinil, m.p. 235° C. (shrinks), 240°-241° C.; [α]$_D^{25°}$+54.1° (c=0.9, MeOH). This product was identical in every respect with the corresponding final product first reported as the dextrorotatory isomer by R. Sarges in Example I of U.S. Pat. No. 4,130,714.

EXAMPLE 29

The procedure described in Example 28 is repeated except that (S)-ethyl 4-amino-6-fluorochroman-4-carboxylate (prepared as described in Example 25) is the starting material employed instead of (S)-methyl 4-amino-6-fluorochroman-4-carboxylate, using the same molar proportions as before. In this particular case, the corresponding final product obtained is (4S)-6-fluoro-spiro-[chroman-4,4-imidazolidine]-2',5'-dione, identical in every respect with the product of Example 28.

EXAMPLE 30

(4S)(2R)-Methyl 4-amino-6-fluoro-2-methylchroman-4-carboxylate (1.84 g., 0.0077 mole), prepared as described in Example 26, and sodium cyanate (1.0 g., 0.015 mole) were stirred in glacial acetic acid (15 ml.) for a period of 20 hours. The resulting solution was then heated at the reflux temperature for a period of four hours and thereafter concentrated in vacuo to afford a residual material. The latter substance was subsequently taken up in ethyl acetate (50 ml.) and the organic solution so obtained was successively washed with separate 25 ml. portions of 1N hydrochloric acid, water, saturated aqueous sodium bicarbonate solution and then brine. The washed organic solution was then dried over anhydrous magnesium sulfate and filtered, and the resulting filtrate subsequently evaporated under reduced pressure to give an oil. Crystallization of the latter material from acetone/hexanes then gave 1.52 g. (79%) of pure (4S)(2R)-6-fluoro-2-methyl-spiro-[chroman-4,4'-imidazolidine]-2',5'-dione (which is 2-methylsorbinil) in the form of a white solid, m.p. 231°-234° C.; [α]$_D^{25°}$+212.2° (c=0.55, MeOH). This product was identical in every respect with the corresponding final product first reported as the dextrorotatory isomer by K. Ueda et al. in Example 1 of Published U.K. Patent Application No. GB 2,080,304A.

EXAMPLE 31

The procedure described in Example 30 is repeated except that (4S)(2R)-ethyl 4-amino-6-fluoro-2-methyl-chroman-4-carboxylate (prepared as described in Example 27) is the starting material employed instead of (4S)(2R)-methyl 4-amino-6-fluoro-2-methylchroman-4-carboxylate, using the same molar proportions as before. In this particular case, the corresponding final product obtained is (4S)(2R)-6-fluoro-2-methyl-spiro-[chroman-4,4'-imidazolidine]-2',5'-dione, identical in every respect with the product of Example 30.

EXAMPLE 32

6-Fluoro-(2R)-methyl-spiro-[chroman-4,4'-2'-phenyl-oxazolidin-5'one] (17 g., 0.055 mole), prepared as described in Example 13, was heated in a mixture of formic acid (70 ml.) and concentrated hydrochloric acid (25 ml.) at the reflux temperature for a period of five hours. The resulting reaction mixture was then stirred at room temperature (~20° C.) for a period of approximately 16 hours (i.e., overnight) and finally concentrated in vacuo to a thick slurry. The latter material, which was essentially crude 4-amino-6-fluoro-(2R)-methylchroman-4-carboxylic acid hydrochloride and benzoic acid, was then diluted with water (100 ml.) and subsequently extracted twice with diethyl ether (2×75 ml.), followed by a further concentration (in vacuo) of the aqueous layer to a volume of 50 ml. The pH of the aqueous concentrate was then adjusted to pH 5.5 with 6N aqueous sodium hydroxide solution and solid sodium cyanate (7.94 g., 0.122 mole) was subsequently added thereto in one portion. After stirring the reaction mixture for a period of 18 hours (at the ambient temperatures), the pH rose to pH 8.8 and was subsequently adjusted to pH 7 with 1N hydrochloric acid. The resulting reaction mixture was then stirred for an additional 24 hours at the ambient temperature. At this point, the spent reaction mixture was filtered through supercel to remove a haze and thereafter cooled to ca. 10° C., followed by a pH adjustment to pH 2.2 with 6N hydrochloric acid. The latter mixture was then stirred for a period of 15 minutes, and the solid material which formed was subsequently collected by means of suction filtration and dried in vacuo to constant weight. In this manner, there were ultimately obtained 10.3 g. of pure 6-fluoro-(2R)-methyl-4-ureidochroman-4-carboxylic acid (63% yield based on the N-benzoyl product of Example 6), m.p. 186°–189° C. (decomp.); IR (KBr) 3485 (s), 3333 (s), 1695 (s), 1620 (s), 1594 (s), 1548 (s), 1485 (s) cm$^{-1}$; NMR (DMSO-d$_6$) (250 MHz) δ 7.3–6.7 (m, 4), 5.6 (d, 2), 4.45 (m, 0.45), 4.15 (m, 0.55), 3.4 (br, H$_2$O), 2.7 (t, 1), 2.2 (dd, 0.55), 1.8 (t, 0.45), 1.35 (dd, 3).

EXAMPLE 33

The procedure described in Example 32 is repeated except that 6-fluoro-(2R)-methyl-spiro-[chroman-4,4'-2'-methyloxazolidin-5'-one] (prepared as described in Example 14) is the starting material employed instead of 6-fluoro-(2R)-methyl-spiro-[chroman-4,4'-2'-phenyloxazolidin-5'one], using the same molar proportions as before. In this particular case, the corresponding final product obtained is 6-fluoro-(2R)-methyl-4-ureidochroman-4carboxylic acid, identical in every respect with the product of Example 32.

EXAMPLE 34

6-Fluoro-(2R)-methyl-4-ureidochroman-4-carboxylic acid (1.5 g., 0.005 mole), prepared as described in Example 32 and 1-(–)-ephedrine (0.925 g., 0.0056 mole) were combined in 6 ml. of 10% aqueous methanol to give a solution. The solvent was subsequently removed therefrom by means of evaporation under reduced pressure to yield a heavy oil, which was thereafter triturated with acetone (10 ml.). Upon completion of this step, the resulting mixture was heated on a steam bath to dissolve the oily salt and as the salt dissolved, crystallized of the desired diastereoisomer commenced. The resulting mixture was then heated for an additonal period of five minutes and finally cooled to room temperature (~20° C.) prior to filtration. The salt collected in this manner was then again heated in acetone (15 ml.) for a period of five minutes, and thereafter was cooled and collected as before. In this way, there was ultimately obtained 0.52 g. (22%) of the pure 1-(–)-ephedrine salt of (4S)(2R)-6-fluoro-2-methyl-4-ureidochroman-4-carboxylic acid, m.p. 199.5°–201° C. (decomp.); [α]$_D^{25}$ +45.7° (c=1.0, MeOH).

Anal. Calcd. for C$_{12}$H$_{13}$FN$_2$O$_4$: C, 61.05; H, 6.98; N, 9.70. Found: C, 60.99; H, 6.60; N, 9.52.

EXAMPLE 35

The procedure described in Example 34 is repeated except that d-(+)-(1-phenylethyl)amine is the reagent of choice employed instead of 1-(–)-ephedrine, using the same molar proportions as before. In this particular case, the corresponding final product obtained is the d-(+)-(1-phenylethyl)amine salt of (4S)(2R)-6-fluoro-2-methyl-4-ureidochroman-4-carboxylic acid.

EXAMPLE 36

The 1-(–)-ephedrine salt of (4S)(2R)-6-fluoro-2-methyl-4-ureidochroman-4-carboxylic acid (1.8 g., 0.047 mole), prepared as described in Example 34, was heated in glacial acetic acid (20 ml.) at the reflux temperature for a period of four hours. The resulting reaction mixture was then filtered to remove some insolubles and the filtrate thereafter concentrated in vacuo to yield a thick slurry. At this point, water (40 ml.) was added to the mixture to precipitate the desired product, which was subsequently recovered by means of suction filtration and air dried to constant weight. The dried solid product was then dissolved in acetone (15 ml.), the organic solution filtered and the filtrate subsequently concentrated in vacuo while adding hexanes thereto to finally give a purified solid product. In this way, there was ultimately obtained 0.54 g. (54%) of pure (4S)(2R)-6-fluoro-2-methyl-spiro-[chroman-4,4'-imidazolidine]-2',5'-dione, m.p. 230°–233° C.; [α]$_D^{25}$ +212° (c=0.5, MeOH); IR (KBr) 3269 (s), 1778 (s), 1720 (s), 1487 (s) cm$^{-1}$; NMR (DMSO-d$_6$)(250 MHz) δ 8.4 (s, 1), 7.1 (dt, 1), 6.9 (m, 2), 4.8 (m, 1), 3.4 (broad s, 1), 2.3 (d, 1), 1.85 (t, 1), 1.35 (d, 3); mass spectrum, (m/e) 250(P+, base peak), 207 (M+—HNCO).

Anal. Calcd. for C$_{12}$H$_{11}$FN$_2$O$_3$: C, 57.65; H, 4.44; N, 11.21. Found: C, 57.70; H, 4.89; N, 10.95.

EXAMPLE 37

The procedure described in Example 36 is repeated except that the d-(+)-(1-phenylethyl)amine salt of (4S)(2R)-6-fluoro-2-methyl-4-ureidochroman-4-carboxylic acid (prepared as described in Example 35) is the starting material employed instead of the corresponding 1-(–)-ephedrine salt. In this particular case, the corresponding final product obtained is (4S)(2R)-6-fluoro-2-methyl-spiro-[chroman-4,4'-imidazolidine]-2',5'-dione, identical in every respect with the product of Example 36.

EXAMPLE 38

The procedure described in Example 28 is repeated except that potassium cyanate is employed in lieu of sodium cyanate as the reagent of choice for the reaction, using the same molar proportions as before. In this particular case, the corresponding final product obtained is 4(S)-6-fluoro-spiro-[chroman-4,4'-imidazolidine]-2',5,-dione, identical in every respect with the procuct of Example 28.

EXAMPLE 39

The procedure described in Example 30 is repeated except that potassium cyanate is employed in lieu of sodium cyanate as the reagent of choice for the reaction, using the same molar proportions as before. In this particular case, the corresponding final product obtained is (4S)(2R)-6-fluoro-2-methyl-spiro-[chroman-4,4'-imidazolidine]-2',5'-dione, identical in every respect with the product of Example 30.

I claim:

1. A process for preparing an (S)-methyl or (S)-ethyl 4-amino-6-fluoro-chroman-4-carboxylate by subjecting 4-amino-6-fluorochroman-4-carboxylic acid or (2R)-4-amino-6-fluoro-2-methylchroman-4-carboxylic acid in the form of a hydrohalide acid addition salt to the sequence of steps comprising:
   (a) esterification with thionyl chloride and the appropriate lower alkanol, followed by basification to form an intermediate racemic methyl or ethyl ester; and
   (b) resolution of said intermediate racemic ester by treatment with α-chymotrypsin to afford the desired (S)-methyl or (S)-ethyl ester in pure form.

* * * * *